(12) United States Patent
Marshall et al.

(10) Patent No.: US 8,103,357 B2
(45) Date of Patent: *Jan. 24, 2012

(54) IMPLANTABLE LEAD INCLUDING SENSOR

(75) Inventors: Mark T. Marshall, Forest Lake, MN (US); Brian T. McHenry, Minneapolis, MN (US); Teresa A. Whitman, Dayton, MN (US); Sandra F. Viktora, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1131 days.

This patent is subject to a terminal disclaimer.

(21) Appl. No.: 11/854,627

(22) Filed: Sep. 13, 2007

(65) Prior Publication Data

US 2008/0004681 A1    Jan. 3, 2008

Related U.S. Application Data (63) Continuation of application No. 10/758,894, filed on Jan. 16, 2004, now Pat. No. 7,286,884.

(51) Int. Cl.
*A61N 1/00* (2006.01)
(52) U.S. Cl. .................................................. 607/116
(58) Field of Classification Search .................. 607/18, 607/116; 600/488
See application file for complete search history.

(56) References Cited

U.S. PATENT DOCUMENTS

| | | |
|---|---|---|
| 3,638,640 A | 2/1972 | Shaw |
| 3,651,454 A | 3/1972 | Venema et al. |
| 3,682,160 A | 8/1972 | Murata et al. |
| 3,717,858 A | 2/1973 | Hadden |
| 3,735,396 A | 5/1973 | Getchen |
| 3,742,473 A | 6/1973 | Hadden |
| 3,805,795 A | 4/1974 | Denniston et al. |
| 3,857,399 A | 12/1974 | Zacouto et al. |
| 3,891,914 A | 6/1975 | Akita |
| 3,922,490 A | 11/1975 | Pettis |
| 3,938,144 A | 2/1976 | Pederson et al. |
| 3,942,536 A | 3/1976 | Mirowski et al. |
| 3,958,558 A | 5/1976 | Dunphy et al. |
| 3,959,772 A | 5/1976 | Wakasa et al. |
| 4,016,480 A | 4/1977 | Hofmann |
| 4,023,562 A | 5/1977 | Hynecek et al. |
| 4,063,220 A | 12/1977 | Metcalfe et al. |
| 4,077,030 A | 2/1978 | Helava |
| 4,093,946 A | 6/1978 | Fowler |
| 4,103,337 A | 7/1978 | Whiteside |
| 4,114,606 A | 9/1978 | Seylar |
| 4,127,845 A | 11/1978 | Dansbach et al. |

(Continued)

FOREIGN PATENT DOCUMENTS

EP    0 235 482    9/1987

(Continued)

OTHER PUBLICATIONS

International Search Report, PCT/US2005/001033, Jun. 23, 2005, 7 Pages.

*Primary Examiner* — George Manuel
(74) *Attorney, Agent, or Firm* — Reed A. Duthler (57) ABSTRACT

An implantable medical lead includes an adaptor coupled to a body of the lead. The adaptor holds a sensor capsule between a first portion and a second portion of the lead body.

22 Claims, 7 Drawing Sheets

U.S. PATENT DOCUMENTS

| | | |
|---|---|---|
| 4,137,910 A | 2/1979 | Murphy |
| 4,139,737 A | 2/1979 | Shinada et al. |
| 4,202,339 A | 5/1980 | Wirtzfeld et al. |
| 4,211,238 A | 7/1980 | Shu et al. |
| 4,227,181 A | 10/1980 | Brittain |
| 4,265,252 A | 5/1981 | Chubbuck et al. |
| 4,266,554 A | 5/1981 | Hamaguri |
| 4,272,758 A | 6/1981 | Giraud |
| 4,293,947 A | 10/1981 | Brittain |
| 4,311,986 A | 1/1982 | Yee |
| 4,360,030 A | 11/1982 | Citron et al. |
| 4,364,397 A | 12/1982 | Citron et al. |
| 4,399,820 A | 8/1983 | Wirtzfeld et al. |
| 4,407,296 A | 10/1983 | Anderson |
| 4,413,250 A | 11/1983 | Porter et al. |
| 4,417,306 A | 11/1983 | Citron et al. |
| 4,420,753 A | 12/1983 | Meyer-Ebrecht et al. |
| 4,422,066 A | 12/1983 | Belcourt et al. |
| 4,432,372 A | 2/1984 | Monroe |
| 4,467,807 A | 8/1984 | Bornzin |
| 4,485,813 A | 12/1984 | Anderson et al. |
| 4,494,950 A | 1/1985 | Fischell |
| 4,519,401 A | 5/1985 | Ko et al. |
| 4,534,025 A | 8/1985 | Floyd |
| 4,535,401 A | 8/1985 | Penn |
| 4,538,262 A | 8/1985 | Sinniger et al. |
| 4,539,992 A | 9/1985 | Calfee et al. |
| 4,543,955 A | 10/1985 | Schroeppel |
| 4,566,456 A | 1/1986 | Koning et al. |
| 4,592,364 A | 6/1986 | Pinto |
| 4,600,017 A | 7/1986 | Schroeppel |
| 4,628,934 A | 12/1986 | Pohndorf et al. |
| 4,671,288 A | 6/1987 | Gough |
| 4,708,143 A | 11/1987 | Schroeppel |
| 4,712,555 A | 12/1987 | Thornander et al. |
| 4,716,887 A | 1/1988 | Koning et al. |
| 4,722,342 A | 2/1988 | Amundson |
| 4,730,389 A | 3/1988 | Baudino et al. |
| 4,730,619 A | 3/1988 | Koning et al. |
| 4,738,267 A | 4/1988 | Lazorthes et al. |
| 4,745,596 A | 5/1988 | Sato |
| 4,750,495 A | 6/1988 | Moore et al. |
| 4,779,199 A | 10/1988 | Yoneda et al. |
| 4,787,389 A | 11/1988 | Tarjan |
| 4,791,935 A | 12/1988 | Baudino et al. |
| 4,794,372 A | 12/1988 | Kazahaya |
| 4,802,481 A | 2/1989 | Schroeppel |
| 4,807,629 A | 2/1989 | Baudino et al. |
| 4,808,994 A | 2/1989 | Riley |
| 4,809,704 A * | 3/1989 | Sogawa et al. ............ 600/488 |
| 4,813,421 A | 3/1989 | Baudino et al. |
| 4,815,469 A | 3/1989 | Cohen et al. |
| 4,821,735 A | 4/1989 | Goor et al. |
| 4,827,933 A | 5/1989 | Koning et al. |
| 4,841,981 A | 6/1989 | Tanabe et al. |
| 4,846,191 A | 7/1989 | Brockway et al. |
| 4,858,615 A | 8/1989 | Meinema |
| 4,860,751 A | 8/1989 | Callaghan |
| 4,867,161 A | 9/1989 | Shaldach |
| 4,867,162 A | 9/1989 | Shaldach |
| 4,867,163 A | 9/1989 | Shaldach |
| 4,873,980 A | 10/1989 | Shaldach |
| 4,877,032 A | 10/1989 | Heinze et al. |
| 4,881,410 A | 11/1989 | Wise et al. |
| 4,886,064 A | 12/1989 | Strandberg |
| 4,903,701 A | 2/1990 | Moore et al. |
| 4,907,022 A | 3/1990 | Myers |
| 4,926,875 A | 5/1990 | Rabinovitz et al. |
| 4,936,304 A | 6/1990 | Kresh et al. |
| 4,941,472 A | 7/1990 | Moden et al. |
| 4,941,473 A | 7/1990 | Tenerz et al. |
| 4,947,854 A | 8/1990 | Rabinovitz et al. |
| 4,967,748 A | 11/1990 | Cohen |
| 4,967,755 A | 11/1990 | Pohndorf |
| 4,984,572 A | 1/1991 | Cohen |
| 4,986,270 A | 1/1991 | Cohen |
| 5,003,976 A | 4/1991 | Alt |
| 5,016,631 A | 5/1991 | Hogrefe |
| 5,021,777 A | 6/1991 | Gross et al. |
| 5,025,786 A | 6/1991 | Siegel |
| 5,040,536 A | 8/1991 | Riff |
| 5,040,538 A | 8/1991 | Mortazavi |
| 5,058,586 A | 10/1991 | Heinze |
| 5,065,759 A | 11/1991 | Begemann et al. |
| 5,076,271 A | 12/1991 | Lekholm et al. |
| 5,085,213 A | 2/1992 | Cohen |
| 5,087,243 A | 2/1992 | Avitall |
| 5,097,831 A | 3/1992 | Lekholm |
| 5,105,810 A | 4/1992 | Collins et al. |
| 5,109,850 A | 5/1992 | Blanco et al. |
| 5,113,859 A | 5/1992 | Funke |
| 5,113,868 A | 5/1992 | Wise et al. |
| 5,129,394 A | 7/1992 | Mehra |
| 5,156,157 A | 10/1992 | Valenta, Jr. et al. |
| 5,166,678 A | 11/1992 | Warrior |
| 5,174,303 A | 12/1992 | Schroeppel |
| 5,184,614 A | 2/1993 | Collins et al. |
| 5,186,169 A | 2/1993 | Shaldach |
| 5,205,286 A | 4/1993 | Soukup et al. |
| 5,207,103 A | 5/1993 | Wise et al. |
| 5,228,176 A | 7/1993 | Bui et al. |
| 5,243,976 A | 9/1993 | Ferek-Petric et al. |
| 5,261,401 A | 11/1993 | Baker et al. |
| 5,265,615 A | 11/1993 | Frank et al. |
| 5,267,564 A | 12/1993 | Barcel et al. |
| 5,275,171 A | 1/1994 | Barcel |
| 5,282,839 A | 2/1994 | Roline et al. |
| 5,293,879 A | 3/1994 | Vonk et al. |
| 5,304,208 A | 4/1994 | Inguaggiato et al. |
| 5,316,001 A | 5/1994 | Ferek-Petric et al. |
| 5,324,316 A | 6/1994 | Schulman et al. |
| 5,324,326 A | 6/1994 | Lubin |
| 5,325,870 A | 7/1994 | Kroll et al. |
| 5,330,505 A | 7/1994 | Cohen |
| 5,336,243 A | 8/1994 | Shaldach |
| 5,336,253 A | 8/1994 | Gordon et al. |
| 5,342,404 A | 8/1994 | Alt et al. |
| 5,353,800 A | 10/1994 | Pohndorf et al. |
| 5,358,514 A | 10/1994 | Schulman et al. |
| 5,365,930 A | 11/1994 | Takashima et al. |
| 5,368,040 A | 11/1994 | Carney |
| 5,391,190 A | 2/1995 | Pederson et al. |
| 5,394,400 A | 2/1995 | Phoy |
| 5,409,009 A | 4/1995 | Olson |
| 5,411,532 A | 5/1995 | Mortazavi |
| 5,417,717 A | 5/1995 | Salo et al. |
| 5,423,869 A | 6/1995 | Poore et al. |
| 5,431,172 A | 7/1995 | Hoegnelid et al. |
| 5,438,987 A | 8/1995 | Thacker et al. |
| 5,451,940 A | 9/1995 | Schneider et al. |
| 5,454,838 A | 10/1995 | Vallana et al. |
| 5,470,348 A | 11/1995 | Neubauer et al. |
| 5,474,574 A | 12/1995 | Saxton et al. |
| 5,488,307 A | 1/1996 | Plott |
| 5,490,323 A | 2/1996 | Thacker et al. |
| 5,496,361 A | 3/1996 | Moberg et al. |
| 5,497,772 A | 3/1996 | Schulman et al. |
| 5,499,627 A | 3/1996 | Steuer et al. |
| 5,507,737 A | 4/1996 | Palmskog |
| 5,518,001 A | 5/1996 | Snell |
| 5,535,752 A | 7/1996 | Halperin et al. |
| 5,549,652 A | 8/1996 | McClure et al. |
| 5,564,434 A | 10/1996 | Halperin et al. |
| 5,569,883 A | 10/1996 | Walter et al. |
| 5,593,430 A * | 1/1997 | Renger ........................ 607/18 |
| 5,628,777 A | 5/1997 | Moberg et al. |
| 5,684,451 A | 11/1997 | Seberger et al. |
| 5,693,075 A | 12/1997 | Plicchi et al. |
| 5,697,958 A | 12/1997 | Paul et al. |
| 5,700,283 A | 12/1997 | Salo |
| 5,701,895 A | 12/1997 | Prutchi et al. |
| 5,702,427 A | 12/1997 | Ecker et al. |
| 5,715,827 A | 2/1998 | Corl et al. |
| 5,722,996 A | 3/1998 | Bonnet et al. |
| 5,722,998 A | 3/1998 | Prutchi et al. |
| 5,725,562 A | 3/1998 | Sheldon |
| 5,735,883 A | 4/1998 | Paul et al. |

| | | |
|---|---|---|
| 5,740,596 A | 4/1998 | Corl et al. |
| 5,741,211 A | 4/1998 | Renirie et al. |
| 5,751,154 A | 5/1998 | Tsugai |
| 5,773,270 A | 6/1998 | D'Orazio et al. |
| 5,782,883 A | 7/1998 | Kroll et al. |
| 5,785,657 A | 7/1998 | Breyer et al. |
| 5,791,344 A | 8/1998 | Schulman et al. |
| 5,792,195 A | 8/1998 | Carlson et al. |
| 5,797,395 A | 8/1998 | Martin |
| 5,810,735 A | 9/1998 | Halperin et al. |
| 5,812,802 A | 9/1998 | Bahout et al. |
| 5,836,987 A | 11/1998 | Baumann et al. |
| 5,843,135 A | 12/1998 | Weijand et al. |
| 5,885,471 A | 3/1999 | Ruben et al. |
| 5,899,927 A | 5/1999 | Ecker et al. |
| 5,902,326 A | 5/1999 | Lessar et al. |
| 5,911,738 A | 6/1999 | Sikorski et al. |
| 5,917,346 A | 6/1999 | Gord |
| 5,918,110 A | 6/1999 | Abraham-Fuchs et al. |
| 5,928,344 A | 7/1999 | Stierli |
| 5,935,081 A | 8/1999 | Kadhiresan |
| 5,936,520 A | 8/1999 | Luitje et al. |
| 5,954,752 A | 9/1999 | Mongeon et al. |
| 5,957,957 A | 9/1999 | Sheldon |
| 5,977,431 A | 11/1999 | Knapp et al. |
| 5,977,803 A | 11/1999 | Tsugai |
| 5,985,129 A | 11/1999 | Gough et al. |
| 5,986,497 A | 11/1999 | Tsugai |
| 5,995,860 A | 11/1999 | Sun et al. |
| 5,999,848 A | 12/1999 | Gord et al. |
| 6,002,963 A | 12/1999 | Mouchawar et al. |
| 6,017,313 A | 1/2000 | Bratteli et al. |
| 6,024,704 A | 2/2000 | Meador et al. |
| 6,025,670 A | 2/2000 | Corl et al. |
| 6,038,475 A | 3/2000 | Sikorski et al. |
| 6,038,480 A | 3/2000 | Hrdlicka et al. |
| 6,070,103 A | 5/2000 | Ogden |
| 6,144,866 A | 11/2000 | Miesel et al. |
| 6,163,723 A | 12/2000 | Roberts et al. |
| 6,501,991 B1 | 12/2002 | Honeck et al. |

FOREIGN PATENT DOCUMENTS

| | | |
|---|---|---|
| EP | 0 356 603 | 11/1993 |
| EP | 1 040 848 A1 | 10/2000 |
| WO | 89/01803 | 3/1989 |
| WO | 90/04942 | 5/1990 |

* cited by examiner

IMPLANTABLE LEAD INCLUDING SENSOR

PRIORITY

The present invention is a continuation of application Ser. No. 10/758,894, filed on Jan. 16, 2004, now U.S. Pat. No. 7,286,884.

TECHNICAL FIELD

The present invention relates to implantable medical electrical leads and more particularly to leads including a physiological sensor and the incorporation thereof along a body of the leads.

BACKGROUND

Cardiac rhythm management (CRM) systems often employ an implantable medical device (IMD) coupled to an endocardial surface of a patient's right heart via one or more medical electrical leads. Typically the one or more leads include electrodes for both stimulating the heart and sensing electrical activity of the heart. Alternatively, or in addition to the electrodes, leads may include means for therapeutic and/or diagnostic fluid infusion. In order to provide better management of cardiac conditions, the one or more leads may also include a physiological sensor. In many cases, it is desirable that all the necessary elements, including electrodes and/or fluid infusion ports and a physiological sensor, be carried on a single lead body wherein locations of each element along the lead body accommodate proper function to meet the therapeutic objectives of the CRM system. In order to accommodate the proper positioning of all the desired elements along a lead body, a sensor assembly includes an adaptor to route conductors past the sensor to additional elements carried by the lead body.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION

The following detailed description is exemplary in nature and is not intended to limit the scope, applicability, or configuration of the invention in any way. Rather, the following description provides a practical illustration for implementing exemplary embodiments of the invention.

Figure 1A:
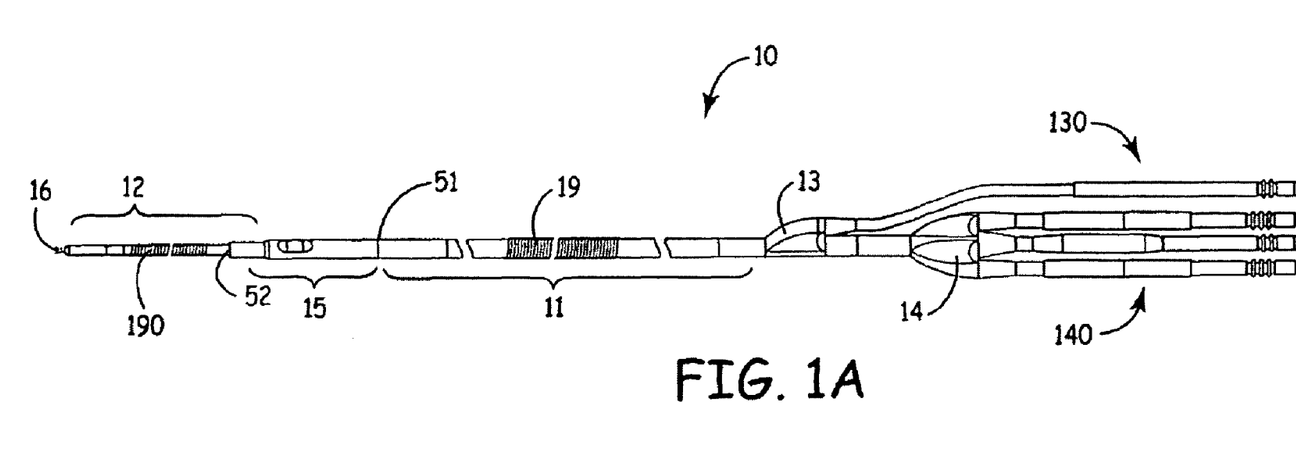
FIGS. 1A-B are plan views of medical electrical leads according to alternate embodiments of the present invention.
Figure 1B:
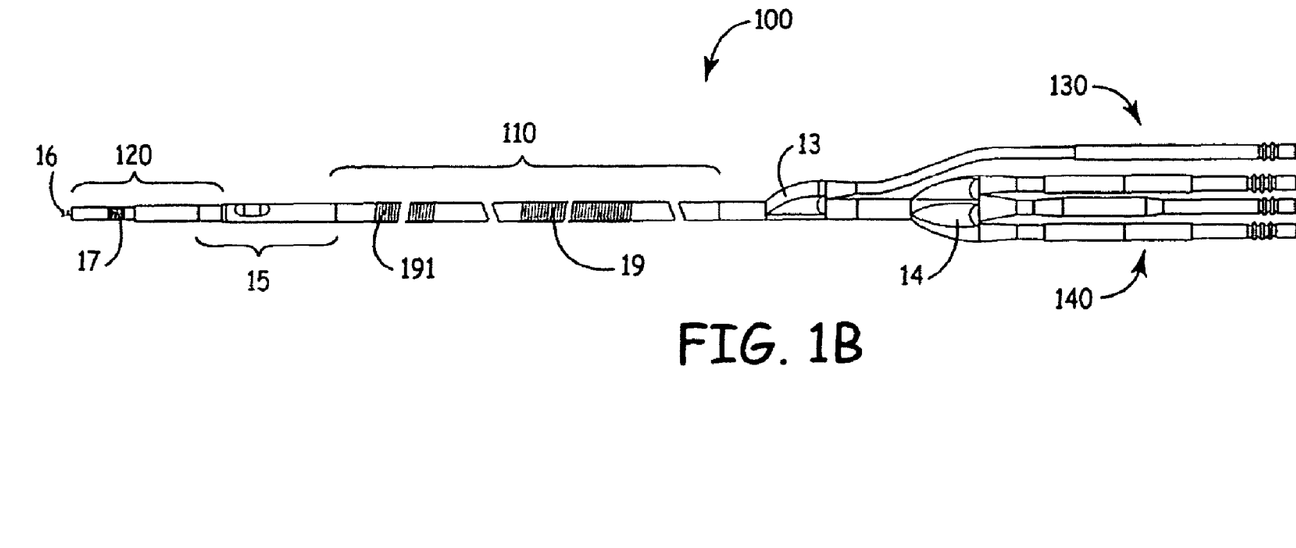

FIGS. 1A-B are plan views of medical electrical leads according to alternate embodiments of the present invention. FIG. 1A illustrates lead 10 including a lead body first portion 11, a lead body second portion 12 and a sensor assembly 15 coupled in between first portion 11 and second portion 12; first portion 11 includes a first high voltage defibrillation electrode 19 and second portion 12 includes a second high voltage defibrillation electrode 190 and a low voltage tip electrode 16. FIG. 1B illustrates lead 100 including a lead body first portion 110, a lead body second portion 120 and sensor assembly 15 coupled in between first portion 110 and second portion 120; in this embodiment, first portion 110 includes first high voltage defibrillation electrode 19 and a second high voltage defibrillation electrode 191 while second portion includes a low voltage ring electrode 17 and low voltage tip electrode 16. Any appropriate low voltage and high voltage electrode designs known to those skilled in the art may be incorporated into embodiments of the present invention, therefore the present invention is not limited to the forms of these electrodes illustrated in FIGS. 1A-B. Although FIGS. 1A-B illustrate first portion 11, 110 including at least one electrode, first lead body portions according alternate embodiments of the present invention need not include any electrodes. Furthermore, according to alternate embodiments, a second lead body portion, i.e. portions 12, 120, may include one or more fluid infusion ports positioned for example where tip electrode 16 or ring electrode 17 are positioned.

FIGS. 1A-B further illustrate lead body first portion 11, 110 joined to a sensor connector leg 130, via a first transition sleeve 13, and to electrode connector legs 140, via a second transition sleeve 14; connector legs 130 and 140 are adapted to electrically couple a sensor of sensor assembly 15 and electrodes 16, 17, 19 and 190/191, respectively to an IMD in a manner well known to those skilled in the art.

Figure 2:
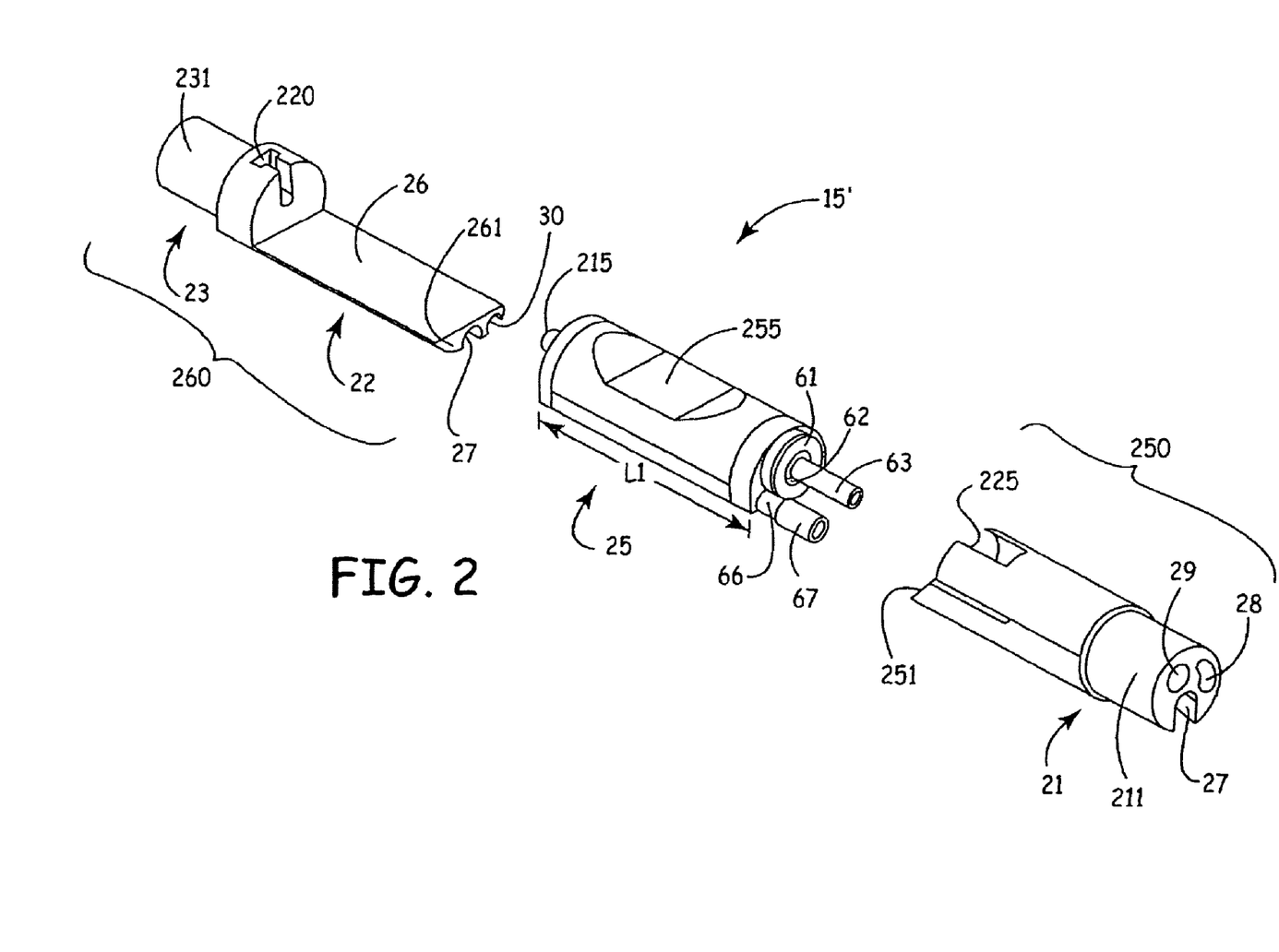
FIG. 2 is an exploded perspective view of a partial sensor assembly according to one embodiment of the present invention.
Figure 3:
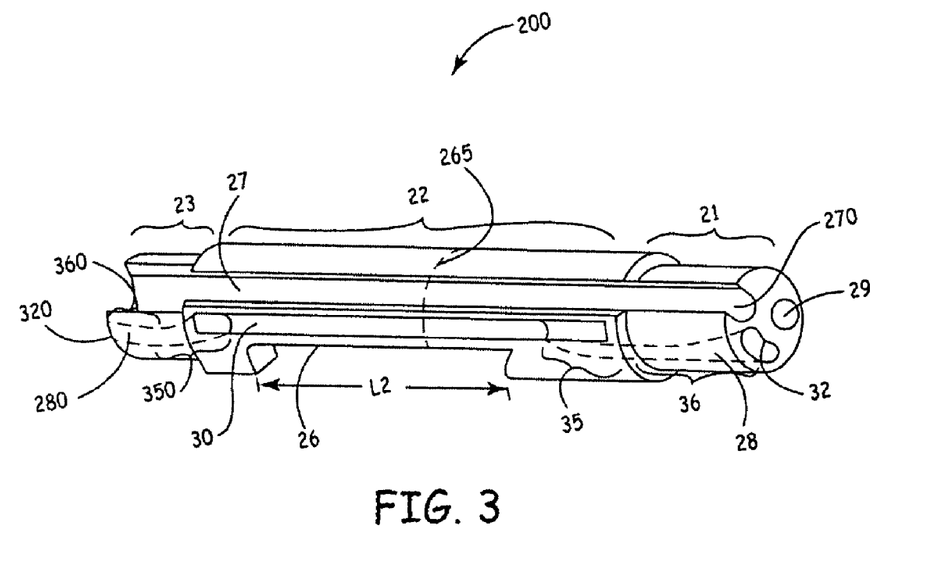
FIG. 3 is a perspective view of an adaptor according to one embodiment of the present invention.

FIG. 2 is an exploded perspective view of a partial sensor assembly 15' according to one embodiment of the present invention and FIG. 3 is a perspective view of an adaptor 200 according to one embodiment of the present invention. FIG. 2 illustrates partial sensor assembly 15' including a sensor capsule 25 and adaptor 200 (FIG. 3); adaptor 200 includes a proximal end 21, a middle portion 22 and a distal end 23, wherein middle portion 22 is formed to hold sensor capsule 25 on a surface 26 when a distal projection 215 of sensor capsule 25 mates/interlocks with a slot 220 included in distal end 23. According to some embodiments of the present invention, sensor capsule 25 includes a sensor selected from a group of physiological sensors, examples of which are well known to those skilled in the art and include, but are not limited to oxygen sensors, pressure sensors, flow sensors and temperature sensors. Commonly assigned U.S. Pat. No. 5,564,434 describes the construction of a pressure and temperature sensor and commonly assigned U.S. Pat. No. 4,791,935 describes the construction of an oxygen sensor; the teachings of the '434 and '935 pertaining to sensor construction are incorporated by reference herein.

Figure 4:
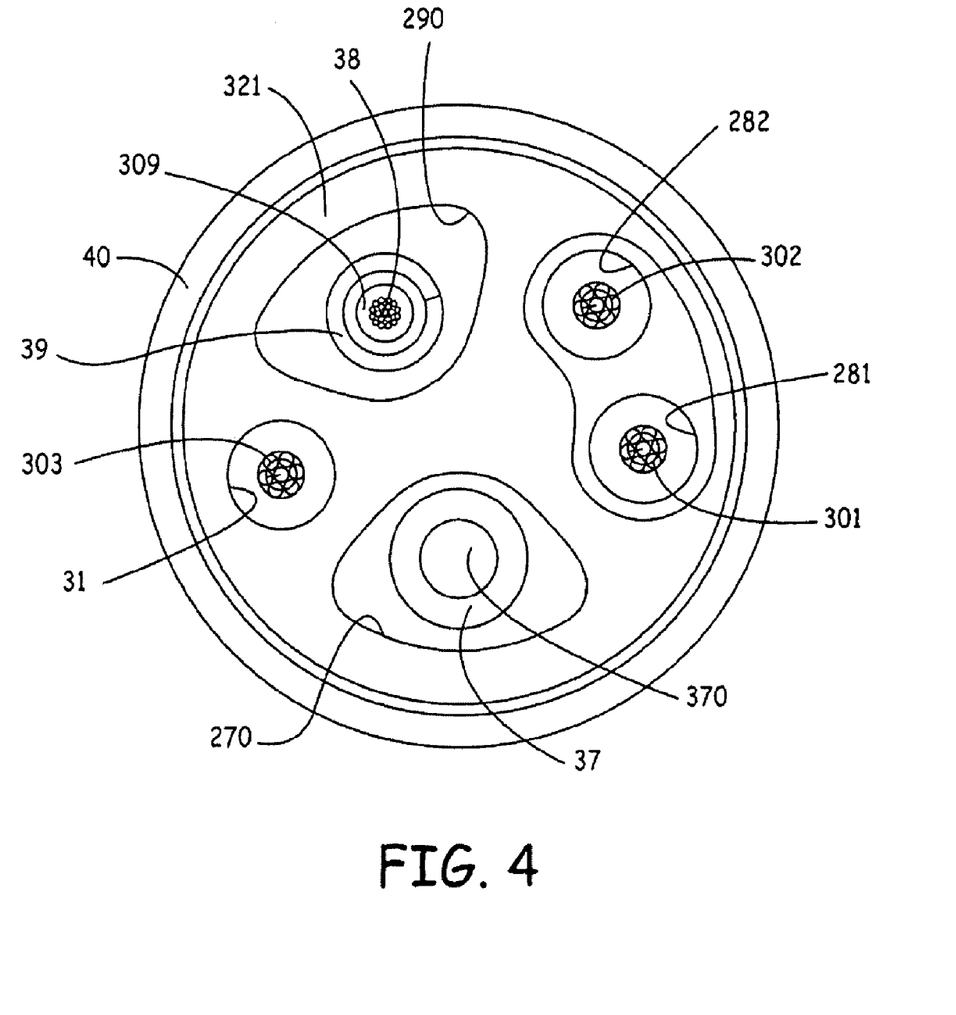
FIG. 4 is a radial section view of a portion of a lead body according to one embodiment of the present invention.

FIG. 2 further illustrates adaptor proximal end 21 including a proximal overlay surface 211 and adaptor distal end 23 including a distal overlay surface 231; surfaces 211 and 231 each mate with a lead body overlay tube 40 (FIG. 4). One tube 40 extends over lead body first portion 11, 110 distally to fit over surface 211 and another tube 40 extends over lead body second portion 12, 120 proximally to fit over surface 231. According to one embodiment of the present invention an outer diameter of overlay tubes 40 is approximately equal to a maximum outer diameter of adaptor 200 so that a relatively smooth transition is made between lead body portions 11, 110, 12, 120 and sensor assembly 15'.

According to another aspect of the present invention, adaptor 200 includes a first part 250 and a second part 260, which are independently formed and subsequently joined together during an assembly process. FIG. 2 illustrates an embodiment wherein a butt joint is formed between a surface 251 of first part 250 and a surface 261 of second part 260, however, according to alternate embodiments, a lap joint or some other type of interlocking joint may be formed between first and second parts 250 and 260. Furthermore, mechanical interlocking, adhesive bonding, solvent welding, ultrasonic welding, laser welding or any combination thereof may join first and second parts 250 and 260. Yet, according to another embodiment a gap may be left between first part 250 and second part 260, which may or may not be filled. Adaptor 200 is formed of any appropriate biocompatible insulative material and, according to one embodiment, comprises molded polyurethane having a hardness of approximately 75 D durometer.

FIGS. 2 and 3 further illustrate adaptor 200 including a first open-sided channel 27 extending through proximal end 21, middle portion 22 and distal end 23; a proximal lumen 28, within proximal end 21, connecting to a second open-sided channel 30, within middle portion 22, which connects to a distal lumen 280, within distal end 23; and a sensor conductor lumen 29, within proximal end 21. According to embodiments of the present invention, open-sided channels 27, 30 and lumens 28, 280, 29 are arranged in adaptor 200 to efficiently route conductors from a proximal portion of a lead body, for example first portions 11, 110 illustrated in FIGS. 1A-B, while isolating conductors from one another and from sensor capsule 25. Embodiments of conductor routing will be described in conjunction with FIG. 4. It should be noted that although channel 30 is illustrated herein and described above as being 'open-sided', according to an alternate embodiment, channel 30 need not be open-sided and, accordingly, lumens 28 and 280 in conjunction with channel 30 form one continuous channel completely surrounded by an inner surface formed in adaptor 200.

FIG. 4 is a radial section view of a portion of a lead body according to one embodiment of the present invention. FIG. 4 illustrates previously described overlay tube 40 about a multi-lumen tube 321 and an arrangement of conductors 37, 38, 39, 301, 302 and 303 in lumens 31, 270, 281, 282 and 290 of the multi-lumen tube 321. Multi-lumen tube 321 is formed of any appropriate insulative and biocompatible material known to those skilled in the art, examples of which include, but are not limited to, polyurethane, silicone and combinations thereof. Overlay tube 40 is formed of any appropriate biocompatible material known to those skilled in the art, examples of which include, but are not limited to, polyurethane, silicone and combinations thereof. Multi-lumen tube 321 may be incorporated in only a proximal portion of the lead body, i.e. first portion 11 or 110 illustrated in FIGS. 1A-B, or in both the proximal portion and a distal portion, i.e. second portion 12, 120 illustrated in FIGS. 1A-B.

According to some embodiments of the present invention, when sensor assembly 15' is coupled to the lead body, a portion of an opening 270 (FIG. 3) of open-sided channel 27 is approximately aligned with lumen 270 thus channel 27 serves to route conductor 37 from lead body first portion 11, 110 to lead body second portion 12, 120. As is further illustrated in FIG. 4, conductor 37 includes a lumen 370; according to one embodiment, conductor 37 includes a coiled electrically conductive wire coupling low voltage tip electrode 16 to one of connector legs 140, while, according to an alternate embodiment, conductor 37 includes a tube wherein lumen 370 is adapted to deliver an infusion of fluid out from a port (not shown) included in distal portion 12, 120 from one of connector legs 140. According to yet another embodiment tip electrode 16 is formed as an extendable/retractable fixation element and conductor 37 conducts a torsional force from one of connector legs 140 to electrode 16 in order to extend or retract electrode 16; such a construction is well known to those skilled in the art. In some embodiments lumen 370 of conductor 37 is sized to accommodate a lead delivery wire, either a stylet or guide wire. According to other embodiments, conductor 37 may not include a lumen at all. Electrically conductive wires used to form some embodiments of conductor 37, and other electrical conductors described herein, may be formed of any applicable biocompatible conductive metal known to those skilled in the art, an example of which includes an MP35N alloy.

FIG. 4 further illustrates a first cabled bundle of electrically conductive wires forming a low voltage conductor 301 extending within lumen 281 and a second cabled bundle of electrically conductive wires forming a high voltage conductor 302 extending within lumen 282. According to one embodiment, for example that illustrated in FIG. 1A, conductor 301 is not included and conductor 302 passes from lead body first portion 11 through adaptor 200 (FIG. 3), via proximal lumen 28, channel 30 and distal lumen 280, to lead body second portion 12 where conductor 302 couples to high voltage electrode 190. According to an alternate embodiment, for example that illustrated in FIG. 1B, conductor 302 extends within lead body first portion 110 and is coupled to high voltage electrode 191 while conductor 301 passes from lead body first portion 110 through adapter 200 (FIG. 3), via proximal lumen 28, channel 30 and distal lumen 280, to lead body second portion 120 where conductor couples to low voltage electrode 17. According to one aspect of the present invention, proximal lumen 28 of adaptor 200, as illustrated in FIG. 3, includes an enlarged opening 32 which communicates with both of lumens 281 and 282 in order to accommodate both of the aforementioned embodiments described in conjunction with FIGS. 1A-B; therefore, a radial orientation of sensor assembly 15 need not be dependent upon a position of the assembly, for example sensor assembly 15 may be incorporated into both embodiments of FIGS. 1A-B without re-orienting the assembly. A dashed line shown in FIG. 4 illustrates a potential alignment of enlarge opening 32 with lumens 281 and 282. FIG. 3 further illustrates distal lumen 280 of adaptor 200 including an enlarged opening 320 to mate in the same manner with lead body distal portions, for example second portions 12 and 120 illustrated in FIGS. 1A-B, according to one embodiment. FIG. 3 also illustrates proximal and distal lumens 28 and 280 including tapered portions 36 and 360 extending from enlarged openings 32 and 320 toward middle portion 22 and ramped transitions 35 and 350 between lumens 28 and 28 and channel 30 according to one embodiment of the present invention.

FIG. 4 further illustrates yet another cabled bundle of electrically conductive wires forming high voltage conductor 303 extending within lumen 31 and a pair of sensor conductors or a sensor bus 600 (FIG. 6B) including a grounded coil conductor 39 formed of one or more electrically conductive wires extending within lumen 290, a carrier cable conductor 38 extending within conductor 39 and an insulative layer 309 formed between conductors 38 and 39. According to embodiments illustrated in FIGS. 1A-B, conductor 303, extends from one of connector legs 140 and within lead body first portion 11, 110 to couple with high voltage electrode 19 and conductors 38 and 39 extend from connector leg 130 within lead body first portion 11, 110 to couple with sensor capsule 25 (FIG. 2). Sensor bus 600 will be described in more detail below, in conjunction with FIGS. 2 and 6A-B.

Figure 5:
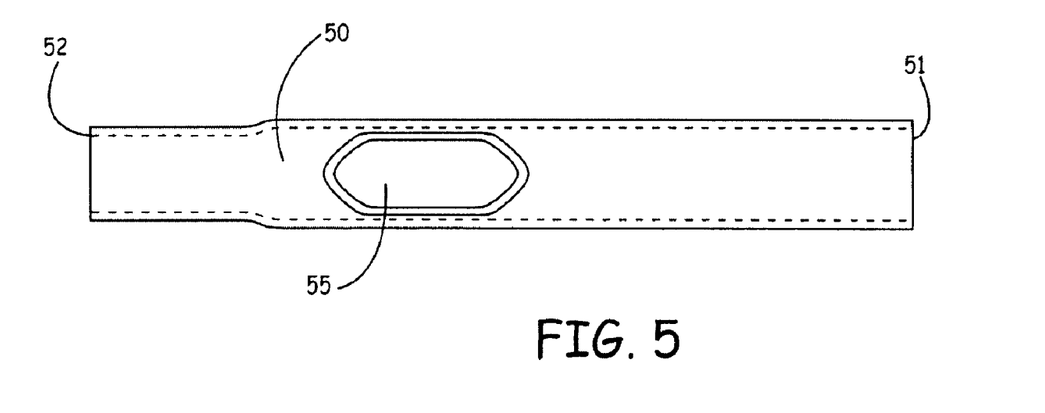
FIG. 5 is a plan view of an outer tube portion of a sensor assembly according to one embodiment of the present invention.

FIG. 5 is a plan view of an outer tube 50 portion of a sensor assembly according to one embodiment of the present invention. FIG. 5 illustrates outer tube 50 including a proximal end 51 and a distal end 52. According to one embodiment of the present invention, with reference to FIGS. 1A-B, 2, 3 and 5, outer tube 50 is positioned about adaptor 200, sensor capsule 25, a junction between adaptor proximal end 21 and lead body first portion 11, 110 and a junction between adaptor distal end 23 and lead body second portion 12, 120. FIG. 5 further illustrates an opening 55 through a sidewall of outer tube 50, which when assembled over sensor capsule 25 will be approximately aligned with an active surface 255 (FIG. 2) of sensor capsule; according to one embodiment, sensor capsule 25 includes a pressure sensor and active surface 255 is a pressure sensitive diaphragm, while according to an alternate embodiment sensor capsule 25 includes an oxygen sensor and active surface is a window facilitating optical transmission.

Figure 6A:
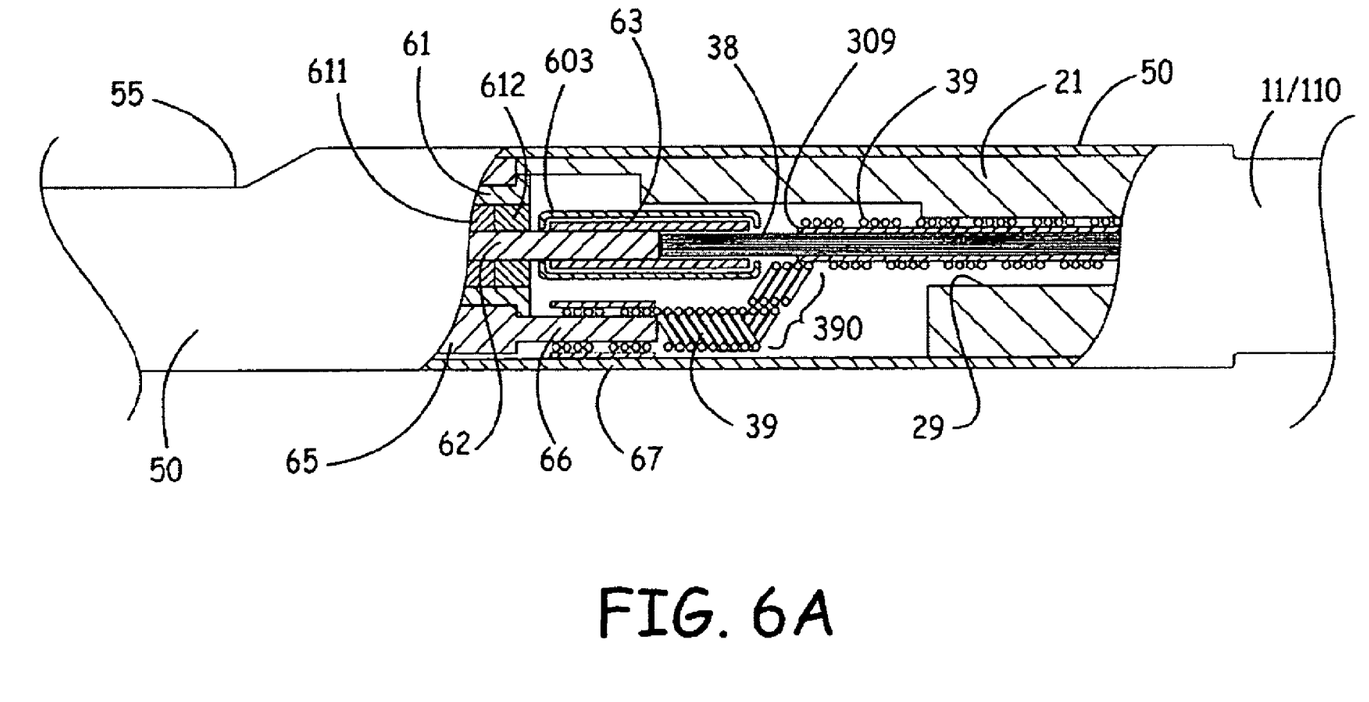
FIG. 6A is a plan view including a partial section of a portion of a lead according to one embodiment of the present invention.

FIG. 6A is a plan view including a partial section of a portion of a lead according to one embodiment of the present invention. FIG. 6A, in conjunction with FIG. 2, illustrates conductors 38 and 39 of sensor bus 600 (FIG. 6B) coupled to sensor capsule 25, wherein carrier cable conductor 38 is coupled to a feedthrough pin 62 via a first crimp sleeve 63 and grounded coil conductor 39 is coupled via a second crimp sleeve 67 to a stud 66, which extends from housing 65. FIG. 6A further illustrates feedthrough pin 62 passing into housing 65 through a feedthrough ferrule 61 and isolated therefrom by an insulator 611 and a backfill 612 according to feedthrough configuration well known to those skilled in the art. According to the illustrated embodiment, sensor capsule 25 may include a pressure sensor and be constructed in a manner similar to that described in U.S. Pat. No. 5,564,434 previously referenced.

As is further illustrated in FIGS. 4 and 6A, conductors 38 and 39 are coaxially arranged wherein grounded coil conductor 39 may serve to electrically shield carrier cable conductor 38. Such shielding minimizes a potential of coupling of electrical signals that may pass back and forth between a body, in which sensor assembly 15 is implanted, and sensor capsule 25; further, if electrical isolation around carrier cable conductor 38 were to break down, there would be a lower impedance pathway between cable conductor 38 and coil conductor 39 than between cable conductor 38 and the body, thereby protecting the body from stimulation via electrical coupling with cable conductor 38 and providing breakdown detection means via electrical coupling between cable 38 and coil 39.

FIG. 6A further illustrates coil conductor 39 including a dog-leg portion 390 extending laterally from a longitudinal axis of coil conductor 39 within lumen 29 of adaptor proximal end 21 to couple with stud 66. As is also illustrated in FIG. 6A, a tubing band insulator 603 is positioned around crimp sleeve 63 in order to assure isolation between coil conductor 39 and crimp sleeve 63.

Figure 6B:
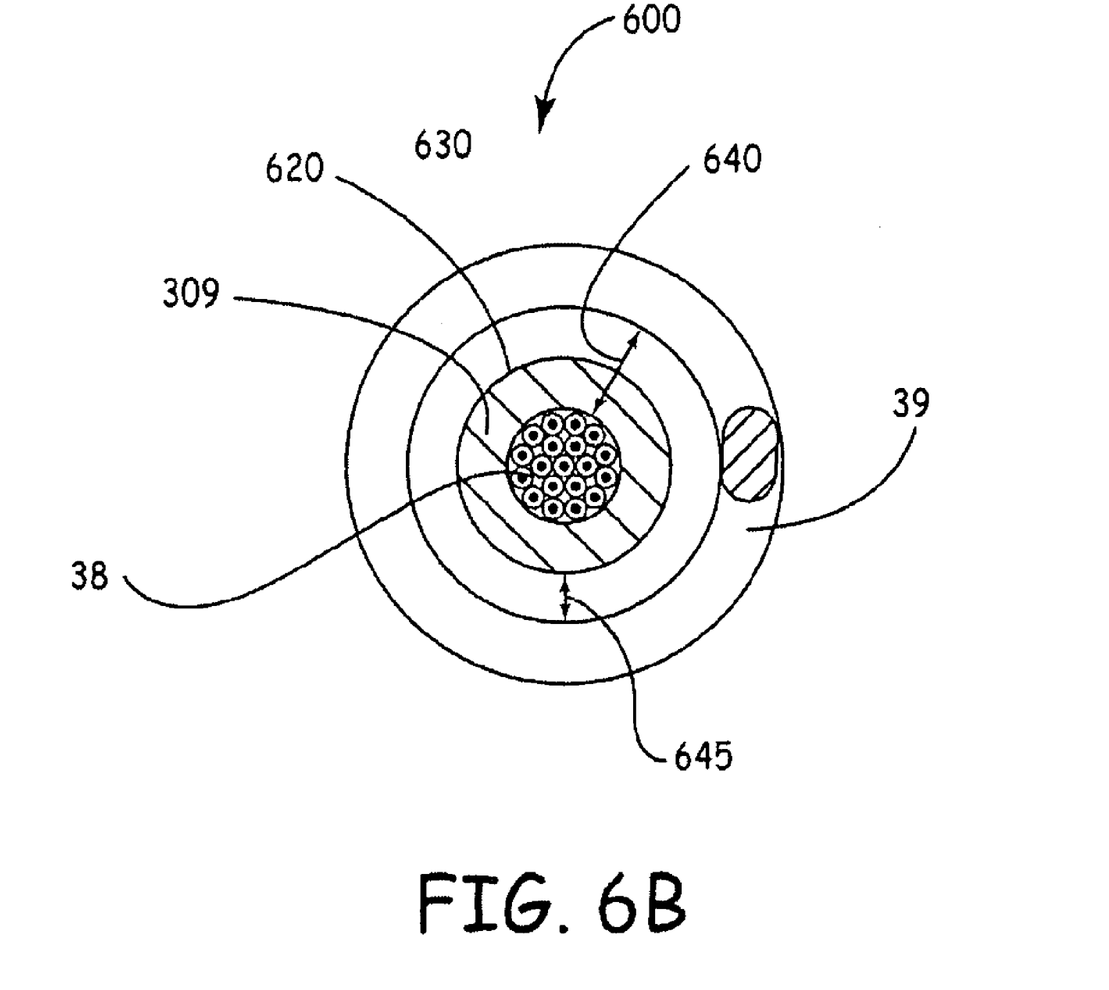
FIG. 6B is a radial section view of a sensor bus according to one embodiment of the present invention.

FIG. 6B is a radial section view of sensor bus 600 according to one embodiment of the present invention. FIG. 6B illustrates insulating layer 309 including an inner diameter 630 and outer diameter 620, a first average gap 640 between cable conductor 38 and coil conductor 39 and a second average gap 645 between layer outer diameter 620 and coil conductor 39. First and second average gaps 640, 645 are defined as radial distances between an outer diameter of cable conductor 38 and insulating layer outer diameter 620, respectively, and an inner diameter of coil conductor 39 when centers of cable conductor 38 and insulating layer 309 are approximately aligned with a center of coil 39 as illustrated in FIG. 6B.

A capacitance of layer 309 is proportional to a relative dielectric coefficient or permittivity of a material forming layer 309 (relative to that of air whose permittivity value is $8.854 \times 10^{-14}$ F/cm, and whose relative dielectric coefficient is 1) divided by the natural log of the ratio of layer outer diameter 620 to layer inner diameter 630. A total capacitance between cable conductor 38 and coil conductor 39 is a series combination of the capacitance of layer 309 and a capacitance of second average gap 645. Since it is desirable to reduce the capacitance between cable conductor 38 and coil conductor 39 in order to reduce current drain during sensing, according to some embodiments of the present invention a relative dielectric coefficient of insulative layer 309 is less than approximately 10, preferably less than approximately 3, and a ratio of layer outer diameter 620 to layer inner diameter 630 is greater than approximately 1.4, preferably greater than approximately 2. According to some embodiments, wherein it is desirable to reduce an overall diameter of a lead body as much as possible, second average gap 645 is minimized, being less than approximately 0.003 inch and preferably less than approximately 0.001 inch.

Although maximizing second average gap 645, being filled with air having a minimum permittivity, would further decrease a capacitance between cable conductor 38 and coil conductor 39, it is recognized that, over the life of an implanted lead, bodily fluid may permeate into a lumen containing sensor bus 600 and fill gap 645. Since bodily fluid has a relative dielectric coefficient of approximately 80, a larger second gap 645 will significantly increase capacitance between conductors 38 and 39. Therefore, in order to keep capacitance low and to reduce drift in capacitance over time, according to some embodiments of the present invention, greater than approximately 50%, preferably 80%, of first average gap 640 is filled with a polymer material having a relative dielectric coefficient less than approximately 10, and preferably less than approximately 3. Although such a polymer material may be insulative layer 309 illustrated herein, the polymer material may fill any portion of first gap 640 in combination with insulative layer 309 to fill the greater than 50% of the first gap 640. Examples of appropriate polymer materials include, but are not limited to, fluoropolymers, silicones, polyimides, urethanes, and any combination thereof.

According to an exemplary embodiment of the present invention, FIG. 6B further illustrates conductor cable 38 including nineteen wires or strands, each formed of an MP35N alloy and divided up into a center strand, six intermediate peripheral strands and twelve outer peripheral strands; each strand of both sets of peripheral strands includes a silver core. According to this embodiment, the center strand has a diameter of approximately 0.0014 inch, the intermediate peripheral strands have a diameter of approximately 0.0013 inch, a left hand lay and a pitch of approximately 0.044 inch, and the outer peripheral strands have a diameter of approximately 0.0012 inch, a right hand lay and a pitch of approximately 0.064 inch; a resulting diameter of conductor 38, according to this embodiment, is between approximately 0.006 inch and 0.007 inch. Insulative layer 309, according to the exemplary embodiment, is formed as a coating of an ETFE fluoropolymer about cable conductor 38 wherein inner diameter is between approximately 0.006 inch and 0.007 inch and outer diameter is between approximately 0.014 and 0.016 inch; ETFE has a relative dielectric coefficient of approximately 3.

Further, conductor 39 according to the exemplary embodiment, formed from five silver cored MP35N wire filars, includes an inner diameter of approximately 0.016 inch and an outer diameter of approximately 0.024 inch. Although exemplary wires incorporated in cable conductor 38 and coil conductor 39 are described as silver-cored MP35N any type of relatively low impedance wire appropriate for implantable leads may be used in embodiments of the present invention. Furthermore a number of wires incorporated within each conductor 38 and 39 can be one or more and of any suitable configuration accommodating a coaxial arrangement of conductors 38 and 39. According to some embodiments, wires of the lowest possible impedance are incorporated into sensor bus conductors 38 and 39 in order to minimize an overall diameter of the sensor bus and to improve shielding characteristics of coil conductor 39.

Referring now to FIGS. 1A-B, 2, 3 and 4 various inventive assembly methods will be described. According to one method, lead body second portion 12, 120 is assembled such that conductor 37, coupled to electrode 16, and either conductor 301, coupled to electrode 17, or conductor 302, coupled to electrodes 90, extend proximally out from second portion 12, 120 to be routed proximally through adaptor 200 and lead body first portion 11, 110 in the arrangement previously described in conjunction with FIG. 4. Alternately, lead body first portion 11, 110 is assembled with the appropriate conductors extending distally therefrom to be routed distally through adaptor 200 and lead body second portion 12, 120. With the conductors appropriately routed, adaptor 200 is joined to lead body first portion 11, 110 and lead body second portion 12, 120 by means of overlapping overlay tubing 40 (FIG. 4) over overlay surfaces 211 and 231 (FIG. 2) as previously described according to one embodiment.

According to one inventive method for assembling sensor capsule 25 into adaptor 200, the aforementioned steps are completed such that adaptor 200 is joined to lead body portions 11, 110 and 12, 120 and the electrode conductors are routed through adaptor 200 and portions 11, 110 and 12, 120 before capsule 25 is mounted. Prior to mounting capsule 25, sensor bus conductors 38 and 39 are coupled to capsule 25, as previously described in conjunction with FIG. 6A, and then placed within lumen 290 (FIG. 4) of lead body first portion 11, 110, having been routed through proximal end 21 (FIG. 2) of adaptor 200.

According to one embodiment, as previously described, adaptor 200 includes a first part 250 and a second part 260 (FIG. 2) which have been independently formed and, according to one inventive assembly method, first and second parts 250 and 260 are joined after capsule 25 is mounted between adaptor proximal end 21 and adaptor distal end 23. As is illustrated in FIGS. 2 and 3, sensor capsule 25 includes a length L1 which much be accommodated by a length L2 of adaptor 200, accordingly an embodiment of adaptor 200 which includes first and second parts 250 and 260 may be tailored to accommodate sensor capsules of varying lengths L1 by adjusting a gap 265 between first and second parts 250 and 260 to vary length L2. Gap 265 may be relatively small to account for tolerance in length L1 of capsule 25 and thus accommodate some of the joining methods previously described, for example adhesive bonding, or may be larger to accommodate different lengths L1 associated with different designs of sensor capsule 25. According to alternate embodiments, only the conductors passing through adaptor 200 and outer tube 50 (FIG. 5) couple first and second parts 250, 260, and some embodiments include an element intervening within gap 265, for example a shim element or a backfill material.

Some final assembly steps, according to one method, include a backfilling process and assembly of outer tube 50. According to one embodiment of the present invention, an area within adaptor and surrounding the coupling of conductors 38 and 39 to sensor capsule 25 is backfilled, for example with silicone medical adhesive, via a backfill opening 225 in adaptor proximal end 21, which is illustrated in FIG. 2. After completing the backfilling step, outer tube 50, which may or may not have been pre-formed to accommodate an underlying contour of sensor assembly 15, is positioned as previously described in conjunction with FIG. 5.

In the foregoing detailed description, the invention has been described with reference to specific embodiments. However, it may be appreciated that various modifications and changes can be made without departing from the scope of the invention as set forth in the appended claims.

What is claimed is:

1. A medical electrical lead, comprising:
a lead body;
a sensor capsule;
an adaptor coupled to the lead body and holding the sensor capsule in the lead body, the adaptor comprising:
an open-sided channel;
a first conductor extending within the lead body and the open-sided channel of the adaptor.

2. The lead of claim 1, wherein the first conductor comprises an electrically conductive coiled wire.

3. The lead of claim 2, wherein the coiled wire includes a lumen sized to accommodate a lead delivery wire.

4. The lead of claim 1, wherein the first conductor comprises a cabled bundle of electrically conductive wires.

5. The lead of claim 1, wherein the first conductor comprises an electrically conductive wire and further comprising a low voltage electrode coupled to the conductor along the lead body.

6. The lead of claim 1, wherein the first conductor comprises an electrically conductive wire and further comprising a high voltage electrode coupled to the conductor along the lead body.

7. The lead of claim 1, wherein the first conductor comprises a fluid infusion tube.

8. A medical electrical lead comprising:
a lead body including a first portion and a second portion, the first portion including a first lumen and a second lumen extending lengthwise therein and the second portion including a first lumen and a second lumen extending lengthwise therein;
a sensor capsule including a length; and
an adaptor coupled to the lead body and holding the sensor capsule in between the lead body portions, the adaptor comprising:
a first part including a proximal end and a proximal lumen,
a second part including a distal end and a distal lumen;
a first open-sided channel extending alongside the sensor capsule.

9. The lead of claim 8, further comprising a first conductor extending within the lead body and the open-sided channel of the adaptor.

10. The lead of claim 9, wherein the first conductor comprises an electrically conductive coiled wire.

11. The lead of claim 10, wherein the coiled wire includes a lumen sized to accommodate a lead delivery wire.

12. The lead of claim 9, wherein the first conductor comprises a cabled bundle of electrically conductive wires.

13. The lead of claim 9, wherein the first conductor comprises an electrically conductive wire and further comprising a low voltage electrode coupled to the conductor along the second portion of the lead body.

14. The lead of claim 9, wherein the first conductor comprises an electrically conductive wire and further comprising a high voltage electrode coupled to the conductor along the second portion of the lead body.

15. The lead of claim 9, wherein the first conductor comprises a fluid infusion tube.

16. A method for assembling a medical electrical lead that includes a lead body first portion, a lead body second portion and a sensor capsule positioned in between the lead body first portion and the lead body second portion, the method comprising the steps of:
    coupling a sensor bus to the sensor capsule;
    coupling an adaptor to the lead body first portion, the adaptor adapted to hold the sensor capsule;
    placing the sensor bus, which extends from the sensor capsule coupling, within a sensor conductor lumen of the lead body first portion through a proximal end of the adaptor; and
    placing a first portion of a first elongate conductor within a first open-sided channel of the adaptor.

17. The method of claim 16, wherein the first conductor comprises an electrically conductive coiled wire.

18. The method of claim 17, wherein the coiled wire includes a lumen sized to accommodate a lead delivery wire.

19. The method of claim 16, wherein the first conductor comprises a cabled bundle of electrically conductive wires.

20. The method of claim 16, wherein the first conductor comprises an electrically conductive wire and further comprising coupling a low voltage to the conductor along the second portion of the lead body.

21. The method of claim 16, wherein the first conductor comprises an electrically conductive wire and further comprising coupling a high voltage to the conductor along the second portion of the lead body.

22. The method of claim 16, wherein the first conductor comprises a fluid infusion tube.

* * * * *